(12) United States Patent
Wu et al.

(10) Patent No.: US 8,953,168 B2
(45) Date of Patent: Feb. 10, 2015

(54) OPTICAL SENSING DEVICES AND METHODS FOR DETECTING SAMPLES USING THE SAME

(75) Inventors: Shu Yuen Wu, Hong Kong (CN); Ho Pui Ho, Hong Kong (CN); Chi-man Lawrence Wu, Hong Kong (CN); Siu-pang Ng, Hong Kong (CN)

(73) Assignees: City University of Hong Kong, Hong Kong (CN); The Chinese University of Hong Kong, Hong Kong (CN)

( * ) Notice: Subject to any disclaimer, the term of this patent is extended or adjusted under 35 U.S.C. 154(b) by 314 days.

(21) Appl. No.: 13/492,444

(22) Filed: Jun. 8, 2012

(65) Prior Publication Data

US 2013/0329230 A1 Dec. 12, 2013

(51) Int. Cl.
*G01B 9/02* (2006.01)

(52) U.S. Cl.
USPC .......................................... 356/491; 356/445

(58) Field of Classification Search
USPC ................................................ 356/445, 491
See application file for complete search history.

(56) References Cited

U.S. PATENT DOCUMENTS

| | | | |
|---|---|---|---|
| 5,055,265 A * | 10/1991 | Finlan | 422/82.05 |
| 5,377,008 A | 12/1994 | Ridgway et al. | |
| 5,412,474 A * | 5/1995 | Reasenberg et al. | 356/486 |
| 5,639,428 A | 6/1997 | Cottingham | |
| 6,161,437 A | 12/2000 | Brennan et al. | |
| 6,421,128 B1 | 7/2002 | Salamon et al. | |
| 6,628,376 B1 * | 9/2003 | Nikitin et al. | 356/38 |
| 6,970,249 B1 | 11/2005 | Lipson et al. | |
| 7,027,676 B2 | 4/2006 | VanWiggeren et al. | |
| 7,394,547 B2 | 7/2008 | Tan et al. | |
| 7,407,817 B2 | 8/2008 | Ho et al. | |
| 7,697,796 B2 | 4/2010 | Kashyap et al. | |
| 7,812,959 B1 | 10/2010 | Kim | |
| 7,892,855 B2 | 2/2011 | Ho et al. | |
| 2003/0152491 A1 | 8/2003 | Kellogg et al. | |
| 2004/0145748 A1 * | 7/2004 | Lee et al. | 356/491 |
| 2004/0259237 A1 | 12/2004 | Kellogg et al. | |
| 2005/0194523 A1 * | 9/2005 | VanWiggeren et al. | 250/225 |

(Continued)

FOREIGN PATENT DOCUMENTS

EP 1 813 683 A1 8/2007

OTHER PUBLICATIONS

S. P. Ng et al., "A White-Light Interferometric Surface Plasmon Resonance Sensor With Wide Dynamic Range and Phase-Sensitive Response," *International Conference on Electron Devices and Solid-State Circuits*, pp. 1-3.

S. P. Ng et al., "White-Light Spectral Interferometry for Surface Plasmon Resonance Sensing Applications," *Optics Express*, vol. 19, No. 5, Feb. 28, 2011, pp. 4522-4525.

(Continued)

*Primary Examiner* — Tarifur Chowdhury
*Assistant Examiner* — Jonathon Cook
(74) *Attorney, Agent, or Firm* — Knobbe, Martens, Olson & Bear LLP

(57) ABSTRACT

An optical sensing device including a source unit configured to generate a polychromatic light beam containing p-polarized beam and s-polarized beam; an interferometric unit configured to introduce birefringent retardation for generating optical path difference between the p-polarized beam and the s-polarized beam; a SPR sensing unit configured to receive both p-polarized beam and s-polarized beam and induce a SPR effect to the p-polarized beam associated with a target sample; and a detection unit for detecting target sample characteristics by obtaining an interference spectrum of the p-polarized beam and the s-polarized beam from the SPR sensing unit.

12 Claims, 10 Drawing Sheets

(56) References Cited

U.S. PATENT DOCUMENTS

| | | |
|---|---|---|
| 2007/0070848 A1 | 3/2007 | Worthington et al. |
| 2007/0077599 A1 | 4/2007 | Krutzik |
| 2009/0086210 A1* | 4/2009 | Ho et al. .................. 356/445 |
| 2010/0238443 A1* | 9/2010 | Claypool et al. ............ 356/369 |
| 2011/0292394 A1 | 12/2011 | Wu et al. |

OTHER PUBLICATIONS

Xudong Fan, et al., "Sensitive optical biosensors for unlabeled targets: A review," Analytica Chimica Acta 620, 2008, pp. 8-26.

Jiri Homola, "Surface Plasmon Resonance Sensors for Detection of Chemical and Biological Species," Chem. Rev. 2008, 108, pp. 462-493.

* cited by examiner

OPTICAL SENSING DEVICES AND METHODS FOR DETECTING SAMPLES USING THE SAME

TECHNICAL FIELD

This application relates to optical devices for chemical and biological detection and methods for detecting samples using the same.

BACKGROUND OF THE INVENTION

Surface plasmon resonance (SPR) has been widely adopted as the promising label-free technique in the area of chemical and biological sensing (Chemical Reviews, 108, 462-493, 2008; Analytica Chimica Acta, 620, 8-26, 2008). It offers the potential to replace the conventional laborious florescence labeling approach for biosensing. In addition, SPR biosensors provide real-time quantitative analysis of bio-molecular interactions through monitoring the optical response in terms of (1) angular reflectivity, (2) spectral characteristics or (3) corresponding phase shift.

U.S. patent application Ser. No. 13/113,837 discloses a wide-dynamic-range phase-sensitive SPR sensor based on the combination of spectral and phase investigation via a differential Michelson spectral interferometer. In this application, a dual-path Michelson interferometer is used to introduce sufficient optical path different (OPD) between the probe and reference paths so that spectral interferogram in terms of sinusoidal fringes can be captured to analyze the SPR phase change between the p- and s-polarized beams. While only the phase change in the p-polarized beam is associated with SPR, the phase change in the s-polarized beam is used as the baseline reference.

However, the Michelson configuration is inherently complicated and requires a dummy SPR prism to be placed in the reference path for dispersion compensation.

SUMMARY OF THE INVENTION

According to an aspect of the present application, an optical sensing device is provided. The optical sensing device includes a source unit configured to generate a polychromatic light beam containing p-polarized beam and s-polarized beam; an interferometric unit, configured to introduce birefringent retardation for generating optical path difference between the p-polarized beam and the s-polarized beam; a SPR sensing unit, configured to receive both p-polarized beam and s-polarized beam and induce a SPR effect to the p-polarized beam associated with a target sample; a detection unit, detecting target sample characteristics by obtaining an interference spectrum of the p-polarized beam and the s-polarized beam from the SPR sensing unit.

According to another aspect of the present application, a method for detecting characteristics of a target sample is provided. The method includes generating, from a source unit, a polychromatic light beam containing p-polarized beam and s-polarized beam; introducing, by an interferometric unit, birefringent retardation for generating optical path difference between the p-polarized beam and the s-polarized beam; introducing a SPR effect associated with the target sample to the p-polarized beam; detecting target sample characteristics by obtaining an interference spectrum of the p-polarized beam and the s-polarized beam from the SPR sensing unit.

DETAILED DESCRIPTION OF THE PREFERRED EMBODIMENTS

Hereinafter, a detailed description will be given with reference to the appended drawings.

Figure 1:
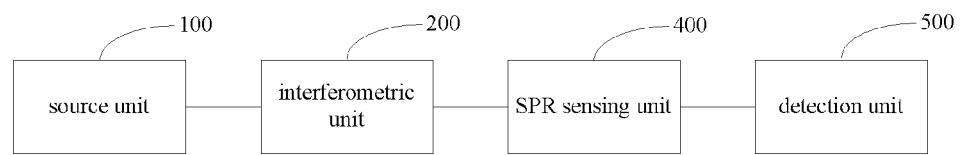
FIG. 1 is a block diagram of an optical device according to an embodiment of the present application.

FIG. 1 illustrates an embodiment of a sensor in accordance with the present application. In the embodiment, the sensor includes a source unit 100, an interferometric unit 200, a SPR sensing unit 400, and detection unit 500. The source unit 100 is configured to generate a polychromatic parallel light beam containing p-polarized beam and s-polarized beam. The interferometric unit 200 includes a common-path interferometric unit 210 for introducing birefringent retardation between the two polarized light beams, so that an optical path difference is generated between the p-polarized beam and the s-polarized beam. The SPR sensing unit 400 is disposed to introduce the SPR effect associated with a target sample to the p-polarized probe beam while keeping the s-polarized reference beam which traverses the same path unaffected. The detection unit 500 is disposed to detect target sample characteristics by obtaining an interference spectrum of the p-polarized beam and the s-polarized beam from the SPR sensing unit.

Figure 2:
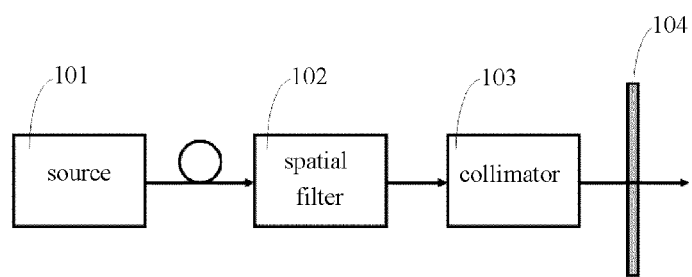
FIG. 2 is a schematic view of a polychromatic light source unit according to an embodiment of the present application.

As shown in FIG. 2, the optical light source unit 100 may comprise a broadband polychromatic electromagnetic radiation source 101, a spatial filter 102, a collimator 103, and a broadband linear polarizer 104.

The source 101 is a broadband polychromatic electromagnetic radiation source which may comprise a quart tungsten halogen (QTH) lamp, a solid state white-light emitting diode (WLED), a broadband superluminescent diode (SLD), a rare-earth-doped amplified spontaneous emission (ASE) source, a supercontinuum laser source for generating supercontinuum by propagation of ultrashort laser pulses in a microstructured optical fiber or any other suitable polychromatic electromagnetic radiation source. The radiation source 101 emits a beam of light containing random polarization components. Here, the use of polychromatic light source can increase the range of incident wavelengths in order to increase the dynamic range of phase-sensitive SPR biosensors.

The spatial filter 102 is provided for selecting the wavelengths of light beam emitted from the source. Optionally, the spatial filter 102 is an adjustable filter for selecting the wavelengths. The collimator 103 transforms the input light beam into parallel beam with planar wavefront. The polarizer 104 is provided to select a content ratio between p-polarized beam and s-polarized beam components of the light source by rotating a polarization angle of the polarizer 104. The polarization angle of the polarizer 104 is set at 45° off to p-polarized beam optical axis to obtain an equal content in both p-polarized beam and s-polarized beam components. The polarization angle can be further adjusted to compensate for the SPR spectral attenuation effect in the probe beam.

Figure 3:
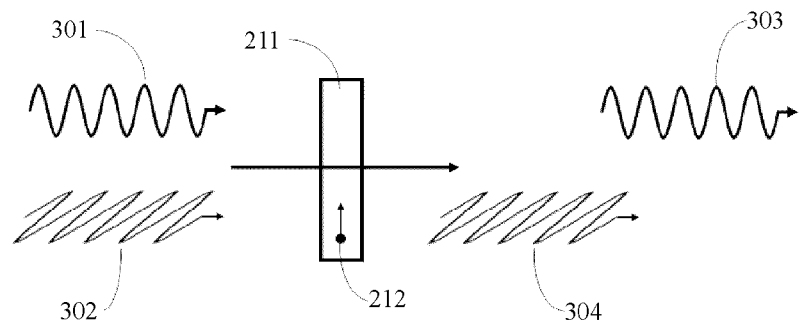
FIG. 3 is a schematic view of the common-path birefringent spectral interferometer according to an embodiment of the present application.

As shown in FIG. 3, the common-path interferometric unit 210 is used to introduce birefringent retardation between the two polarized light beams, so that an optical path difference is generated between the p-polarized probe beam 301 and the s-polarized reference beam 302. As shown in FIG. 3, the interferometric unit 210 may be a typical birefringent interferometer, which contains a broadband birefringent optical crystal 211. The orthogonal birefringent axes 212 of crystal 211 represent the ordinary ray (o-ray, arrow in upwards direction) and extra-ordinary ray (e-ray, dot in the direction perpendicular to the screen) respectively. The axes 212 are set in accordance with the incoming respective p-polarized beam 301 and s-polarized beam 302 for the birefringent optical path difference to be implemented correctly. For example, prior to traversing the crystal 211, p-polarized beam 301 and s-polarized beam 302 have zero optical path difference (OPD) as shown in FIG. 3. With birefringent axes 212 adjusted in line with respective polarized beams, i.e. p-polarized beam corresponds to the ordinary ray whereas s-polarized beam corresponds to the extra-ordinary ray, the two polarized beams experience different optical paths as they traverse the birefringent crystal. After passing the crystal 211, the p-polarized beam 301 and the s-polarized beam 302 become p-polarized beam 303 and the s-polarized beam 304 with optical path difference (OPD). The retardation between the two polarized beams 303 and 304 due to birefringent crystal 211 is demonstrated in FIG. 3. The amount of retardation can be controlled by the thickness of the optical crystal 211. The thickness of the optical crystal 211 is designed to introduce a sufficient OPD between the two polarized beams, so that adequate spectral oscillation can be observed for signal analysis. On the other hand, the thickness of the optical crystal 211 is also designed to avoid aliasing of the signal to be resolved by the spectrometer.

According to an embodiment, the interferometric unit 200 may further include a carrier frequency modulation unit 220 for introducing an extra OPD between the p-polarized beam and the s-polarized beam from the common-path interferometric unit 210.

Figure 4:
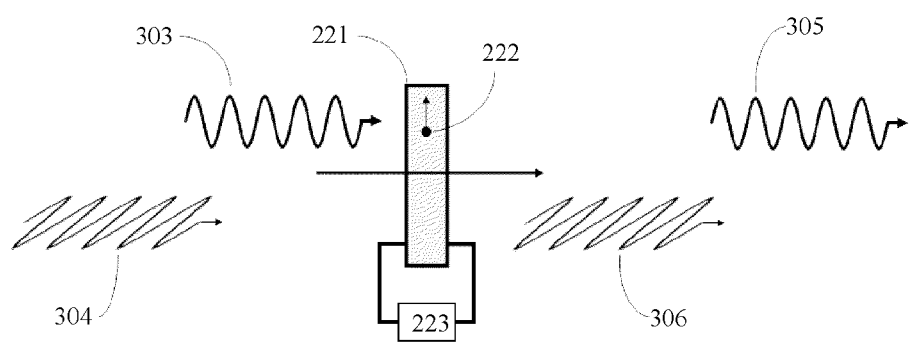
FIG. 4 is a schematic view of the electronically controlled liquid crystal variable retarder according to an embodiment of the present application.

The carrier frequency modulation unit 220 is illustrated in FIG. 4. The carrier frequency modulation unit 220 may include a liquid crystal variable retarder 221 and an electronic controller 223. The liquid crystal variable retarder 221 is used to introduce an extra OPD between the p-polarized beam and the s-polarized beam at each wavelength. The electronic controller 223 is used to control the amount of the extra OPD introduced by the liquid crystal variable retarder 221.

The orthogonal birefringent axes 222 of the liquid crystal variable retarder 221 are aligned according to the respective polarized beams. The carrier frequency modulation unit 220 may generate oscillation cycles in the time domain. It is possible to process these temporal oscillations through existing demodulation algorithm while there is a spectral oscillation discontinuity due to optimized SPR/LRSPR condition in the optical spectrum. As illustrated in FIG. 4, the incoming s-polarized beam 304 experiences an extra retardation against the p-polarized beam 303 as both polarized beams traverse the liquid the crystal retarder 221 electronically controlled by the electronic controller 223. As shown in FIG. 4, after passing the retarder 221, an extra three-quarters of a wavelength behind is introduced between the s-polarized beam 306 and the p-polarized beam 305. The extra retardation may be precisely adjusted linearly via the application of an external voltage or current source controlled by the controller 223.

The sensing unit 400 is disposed to receive the p-polarized beam 303 or 305 and the s-polarized beam 304 or 306 for introducing the SPR effect associated with a target sample to the p-polarized probe beam.

Figure 8:
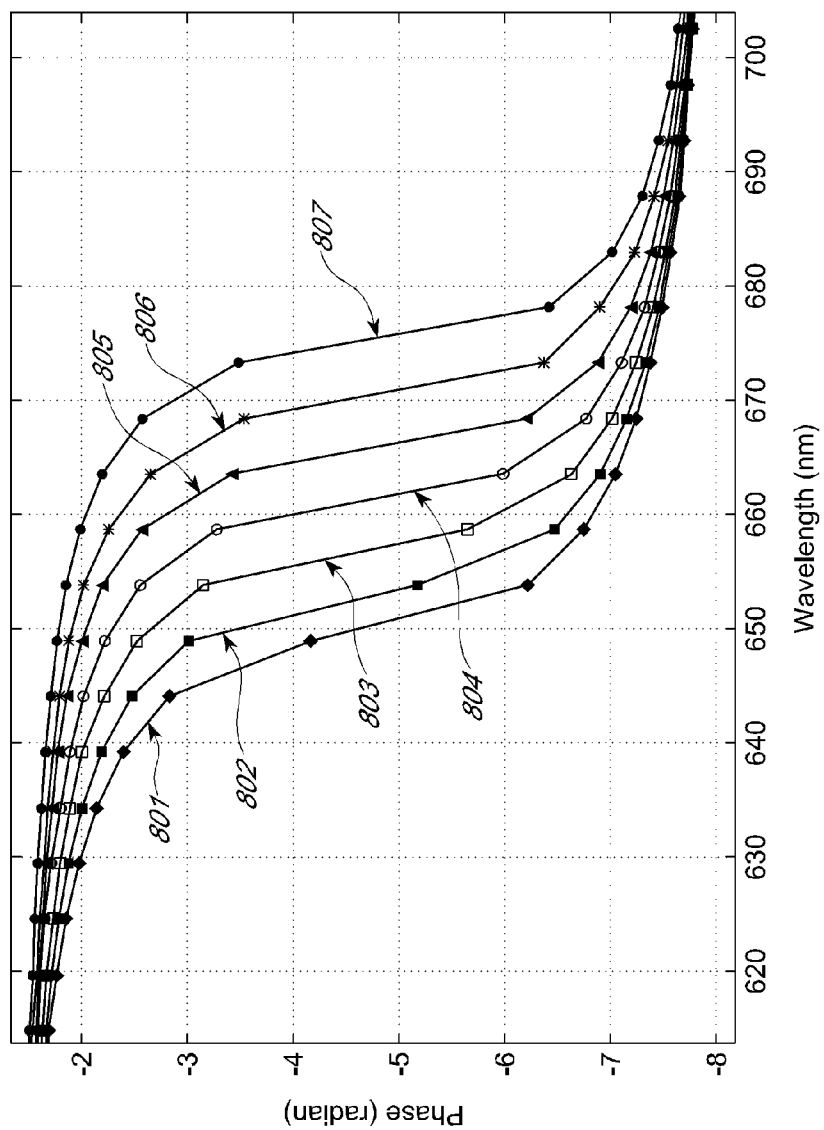
FIG. 8 shows the differential spectral phase results of SPR sensing surface configuration obtained from experiment with sodium chloride solution of various concentrations: 0%, 2%, 4%, 6%, 8%, 10%, and 12% by weight.

In an embodiment, the sensing unit 400 is a conventional SPR sensing unit. To demonstrate the wide dynamic range of the present application, an experiment using the dielectric/metal/dielectric SPR sensing structure has been conducted. A triangular prism made of BK7 glass is employed. In the conventional SRR configuration, the transducing layer of the sensing surface is made of conducting material such as gold. In this case, a gold thin layer, nominally 48 nm thick, is employed because of its good chemical resistance. The target samples are sodium chloride solutions. The concentrations of these solutions are from 0% to 12% (from curve 801 to curve 807 in FIG. 8) by weight with 2% increment, the corresponding refractive index unit (MU) ranged from 1.3330 to 1.3541. As seen from these plots, the system covers a dynamic range of $2 \times 10^{-2}$ MU with spectral range covering 600 nm to 800 nm.

Figure 5:
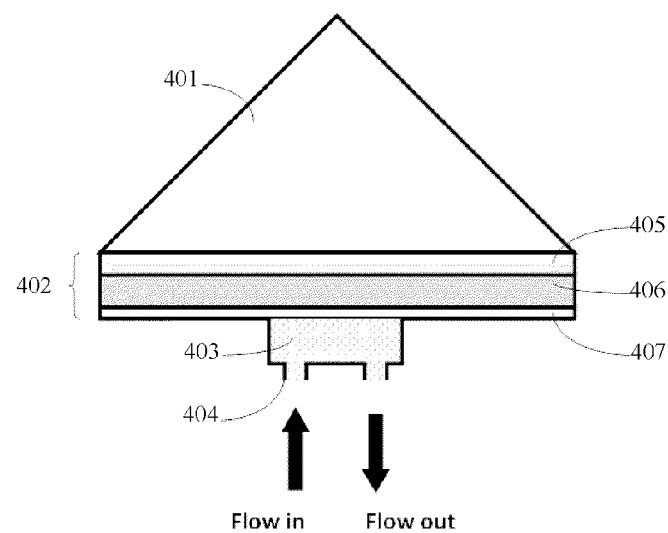
FIG. 5 is a schematic view of an LRSPR sensing surface configuration according to an embodiment of the present application.

In another embodiment, the sensing unit 400 is a prism coupling scheme for LRSPR configuration (prism/metal layer/dielectric layer/metal layer/sample) are used and the configurations thereof are shown in FIG. 5. In LRSPR configuration, the prism coupling scheme comprises a prism 401, a transducing layer of the sensing surface 402 is made of a dielectric layer 406 which is sandwiched by two conducting material 405 and 407 such as gold or silver on the prism 401, and a sample flow chamber 404 associated with the prism 401 for guiding a sample 403 flowing over the sensing surface 407. The prism 401 can be made of transparent dielectric material such as plastic or glass in order to enhance the momentum of light to match with the momentum of SPW. In an embodiment, a right-triangle prism made of BK7 glass is employed. In the embodiment, the first layer of the conducting material 405 from the prism surface is gold with a thickness of 48 nm. The second layer of the dielectric material 406 is silicon dioxide with a thickness of 453 nm. The third layer of the conducting material 407 is gold with a thickness of 2 nm. The choice of thickness for the layers depends on applications and material selection. The sample flow chamber 404 is designed to permit the sample 403 flowing in and out of the chamber 404 while making contact with the sensing surface. The introduction of LRSPR effect in the SPR sensing surface can sharpen the resonance peak so that the detection resolution of phase-sensitive SPR biosensors can be further enhanced. The sample 403 is normally used in aqueous form. Sodium chloride solutions in the concentration of weight percentage from 0% to 12% with 2% increments were used in the experimental demonstration.

For the s-polarized beam as reference, it traverses exactly the same optical components via the common path except that it is not affected by the SPR unit 400. The reference s-polarized beam enable spectral interference with the p-polarized beam which has undergone resonance with SPW and may be used to increase the mean intensity of the resolved spectral oscillation therefore the detection unit 500 can acquire sufficient optical signal for further processing.

Figure 6:
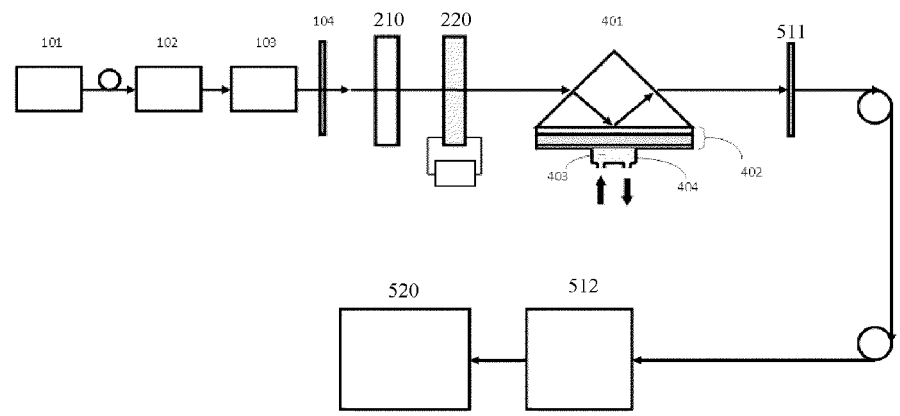
FIG. 6 is a schematic view of an optical device according to an embodiment of the present application.

As shown in FIG. 6, the detection unit 500 may include an optical probe unit 510 and a processing unit 520.

In an embodiment, the optical probe unit 510 includes a broadband linear polarizer 511 and a prober 512. The broadband linear polarizer 511 is adjusted to recombine the p- and s-polarized beams from the SPR sensing unit so as to generate spectral interferograms. The prober 512 is configured to obtain the interference spectrum of the recombined light beam.

The prober 512 may contain a single channel spectral analyzer 513 which may comprise a dispersive grating for separating a light beam into spatially dispersed wavelengths; and a detector array 514 have a plurality of pixels, each pixel for measuring an intensity oscillation signal for a wavelength of the dispersed wavelengths. The detector array 514 may be a linear charge-coupled device (CCD) detector array used to capture the spectral intensity oscillation of the recombined p- and s-polarized beams. The signal trace from the entire optical detector array 514 contains all the information required for computing the spectral phase change and spectral intensity dip due to energy transformation associated with the SPR effect at all incident wavelengths at fixed angles.

Figure 7A:
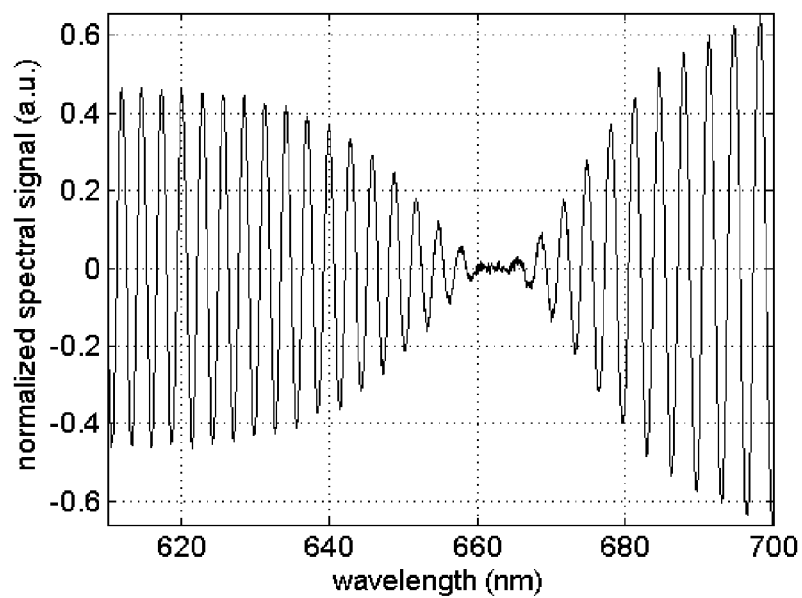
FIG. 7a is the normalized spectral oscillation with LRSPR signal obtained from an embodiment of the present application.

The intensity recorded by each pixel on the detector array is a channeled interference spectrum as shown in FIG. 7a which can be described by the following equation $$I(\lambda) = I_0(\lambda)\left\{1 + V(\lambda)\cos\left[2\pi\left(\frac{OPD_\lambda}{\lambda}\right) + \varphi_{SPR}\right]\right\},$$

where $I_0(\lambda)$ is the reference spectrum, $V(\lambda)$ is the visibility of the spectral fringe, and $OPD_\lambda$ is the wavelength dependent birefringent retardation introduced by the common-path interferometric unit (for example, YVO4 crystal), $\phi_{SPR}$ is the spectral phase information directly associated with the SPR condition of the target sample. With the change of SPR wavelength due to refractive index alternation and a fixed birefringent retardation introduced between the two polarized beams, the phase term $\phi_{SPR}$ can be extracted with appropriate signal processing method to determine the change of refractive index.

Figure 7B:
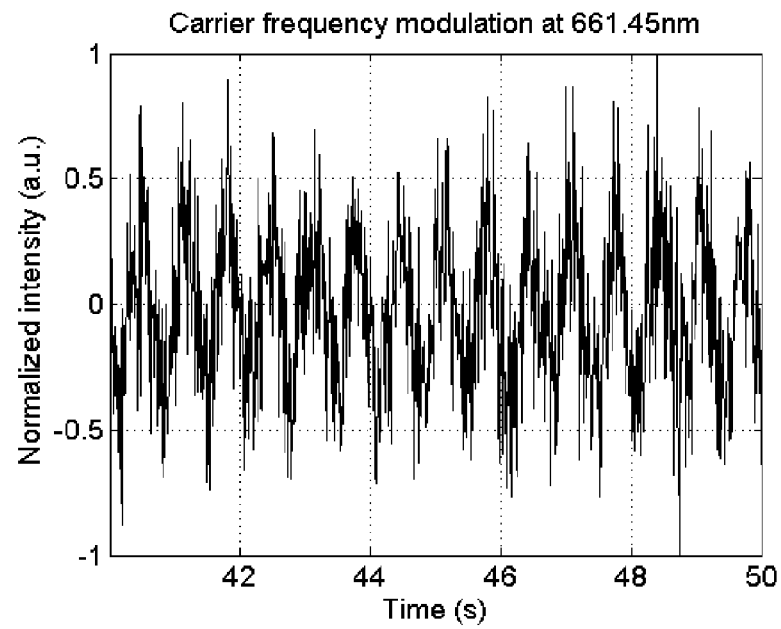
FIG. 7b is the normalized carrier-frequency-modulation LRSPR signal obtained from an embodiment of the present application.
Figure 7C:
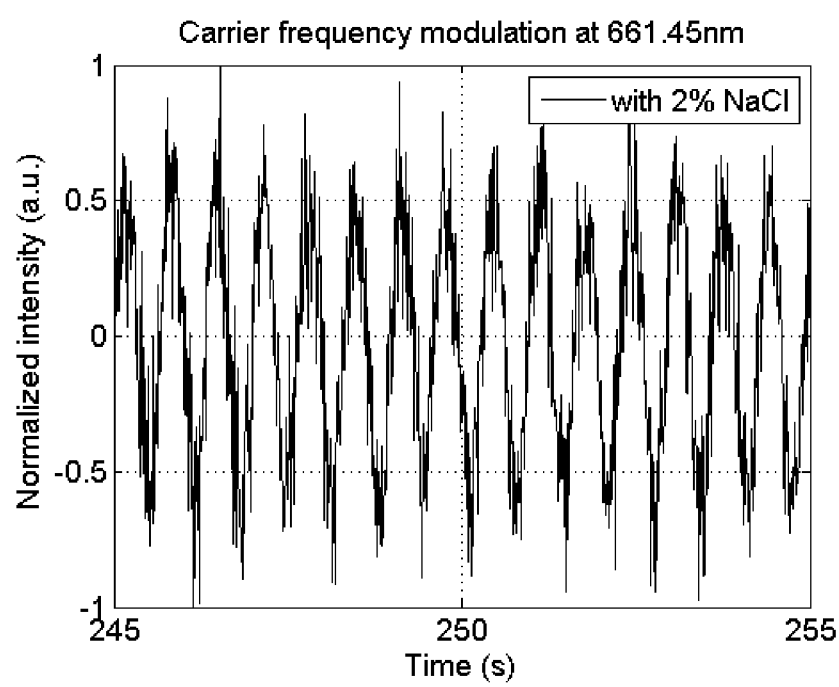
FIG. 7c is the normalized carrier-frequency-modulation LRSPR signal obtained from an embodiment of the present application.

When the carrier frequency modulation technique is implemented, the intensity signal will reflect the phase stepping introduced by the retarder 221. For example, the retardation of the liquid crystal variable retarder 221 is alternated by the electronic controller 223. That is, the carrier frequency modulation 220 can introduce a time delay between the p-polarized and s-polarized components up to a for all the wavelengths interrogated before the polarized beams recombine at the exit of the interferometric path to the detection unit 500, so that each pixel of the detector array of the prober 512 can detect its own temporal oscillation. That is, the optical detector pixel array can be a high density linear charge-coupled optoelectronic detector array for capturing the spectral oscillation change induced by the SPR sensing unit; and the digitized carrier-frequency-modulated interferograms can be stored so as to compute the pixel-wise differential phase change between the p- and s-polarized SPR beams at certain small time interval. As shown in FIGS. 7b and 7c, the temporal oscillation serves to provide extra data points so that the spectral phase at vicinity to the exact SPR wavelength can be evaluated with higher degree of accuracy. The carrier frequency modulation technique can be understood as $$I(\lambda) = I_0(\lambda)\left\{1 + V(\lambda)\cos\left[2\pi\left(\frac{OPD_\lambda}{\lambda}\right) + \varphi_{SPR} + \varphi_{carrier}\right]\right\},$$

where $\phi_{carrier}$ is the time delay introduced by the liquid crystal variable retarder 221. Therefore, each pixel on the spectral CCD array of the prober 512 contains its own oscillation in the time domain. The SPR phase information is however preserved so that the differential phase can be extracted along the temporal dimension. Therefore, the higher the number of temporal cycle, the better is the accuracy of SPR phase extraction. FIGS. 7b and 7c shows the addition of the electronic controlled liquid crystal variable retarder implemented according to an embodiment.

The spectral intensity oscillation signals of the interference between p-polarized and s-polarized beams from the probe unit 510 can be processed by the processing unit 520 to determine the target sample characteristics by computing differential phase between the p-polarized and s-polarized beams to detect a refractive index change associate with the target sample. The processing unit 520 may comprise a personal microcomputer or any other processor. It is employed to compute the differential phase between p-polarized beam and s-polarized beam directly. Subsequently, the refractive index change associated with the binding of biomolecules to the sensor surface can be found.

Figure 9:
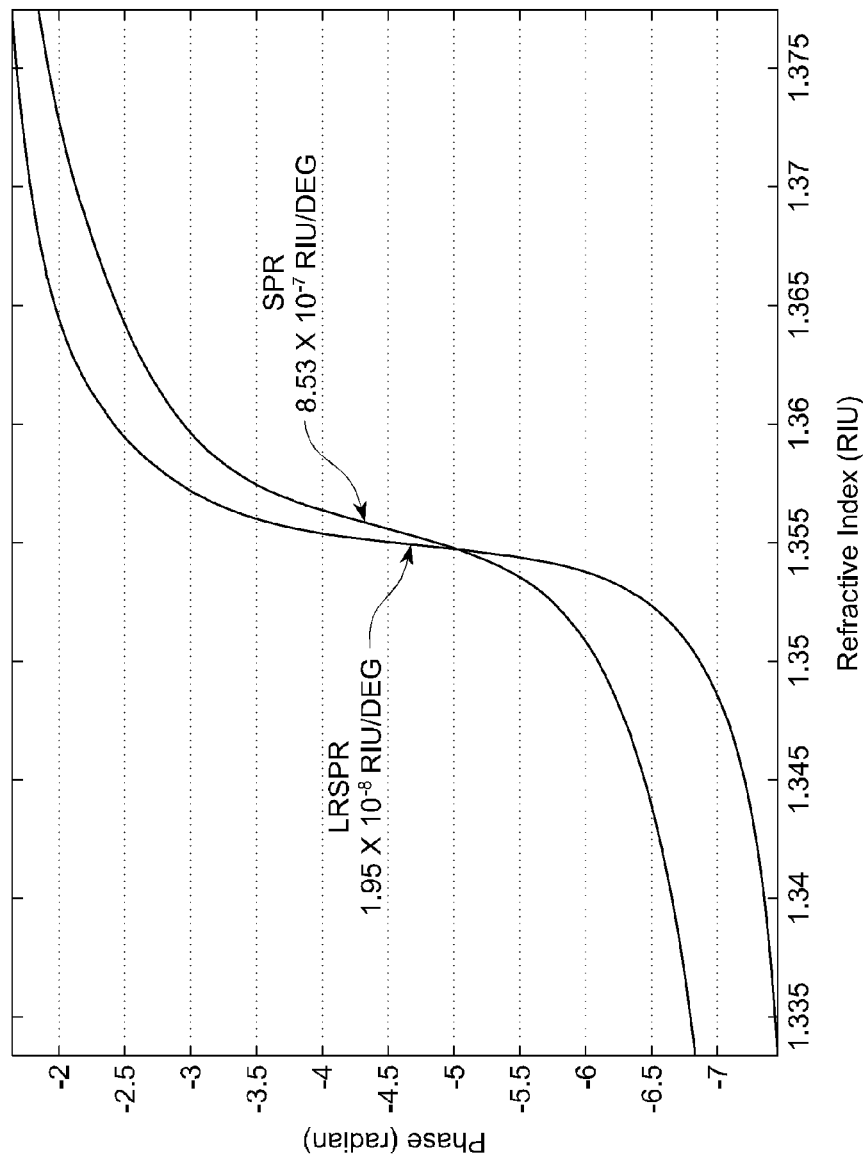
FIG. 9 shows the simulation results of the phase response in SPR and LRSPR sensing surface configuration.
Figure 10:
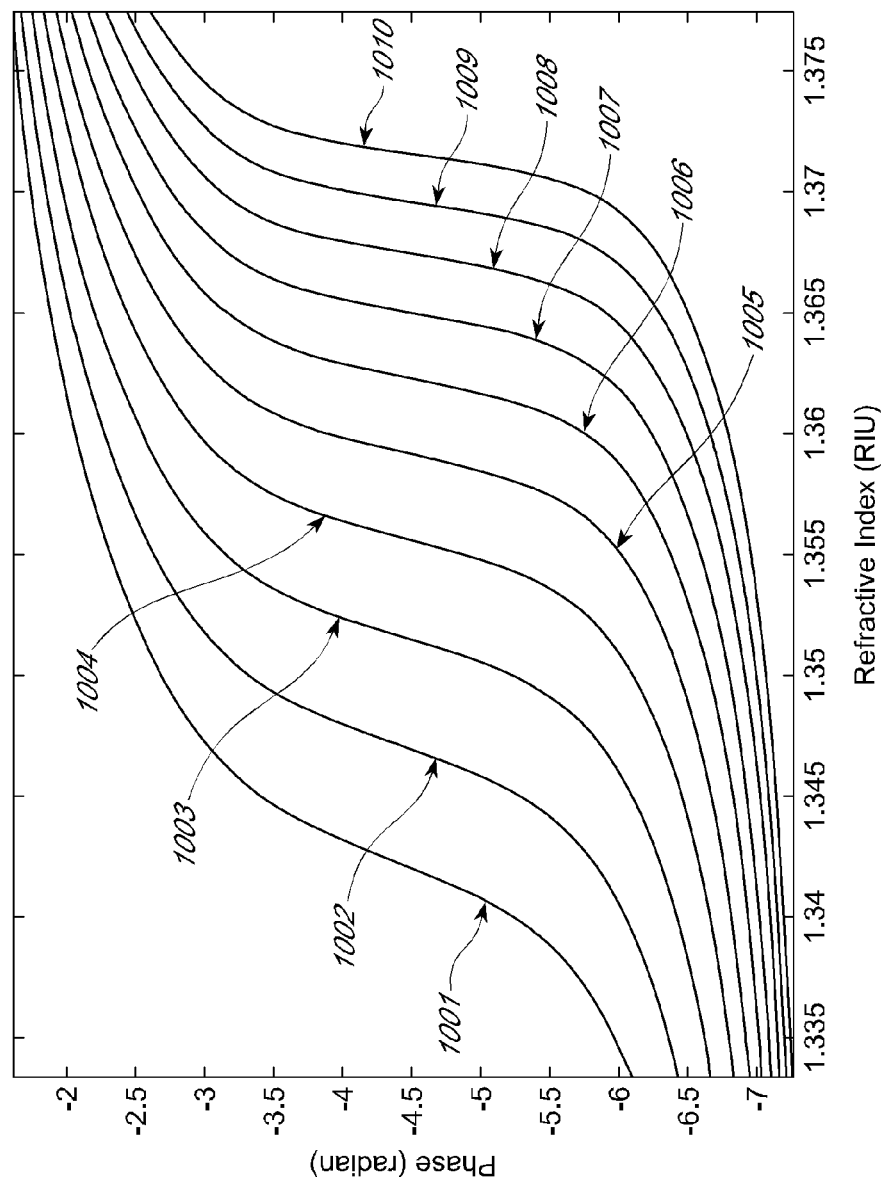
FIG. 10 shows the simulation results of the phase response in the wide dynamic range spectral phase-sensitive SPR sensor with the SPR sensing surface configuration.
Figure 11:
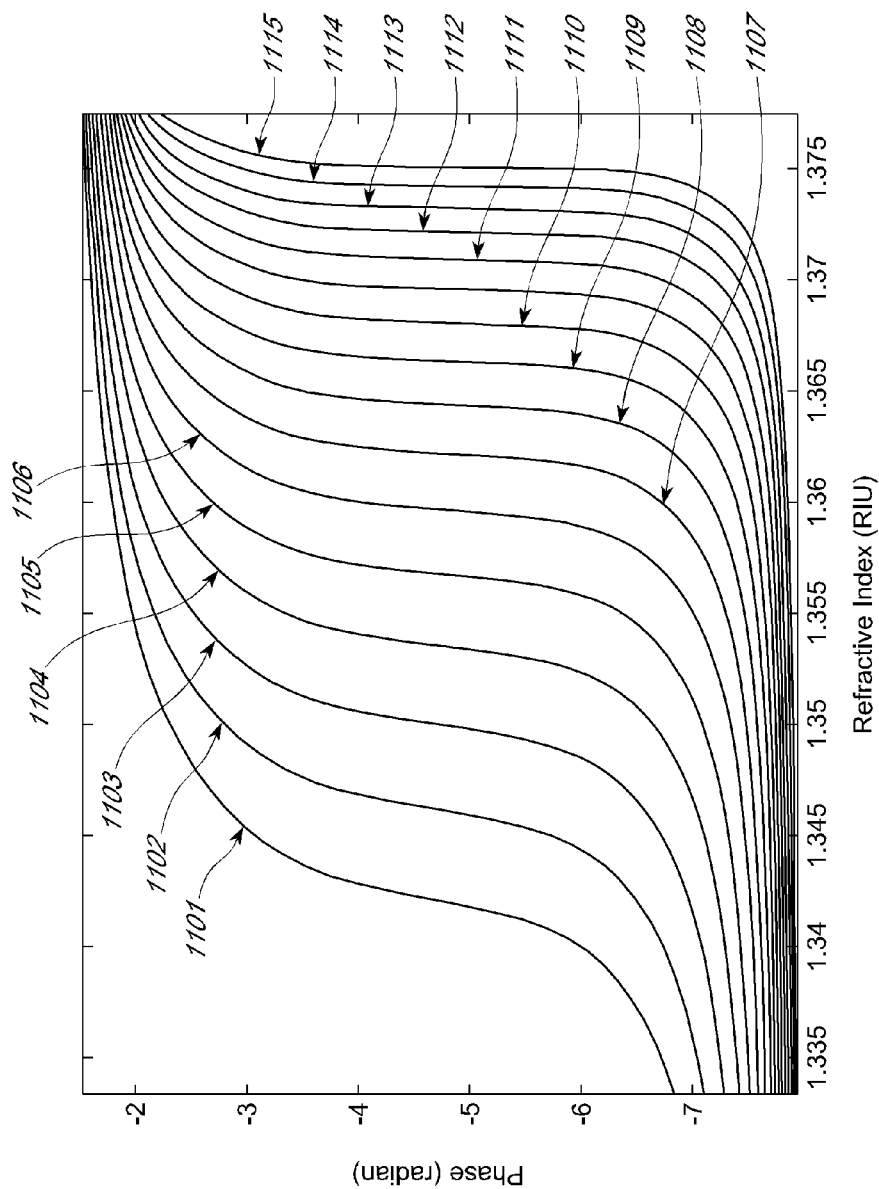
FIG. 11 shows the simulation results of the phase response in the wide dynamic range spectral phase-sensitive SPR sensor with the LRSPR sensing surface configuration.

Simulation results for the phase responses of the optical sensing device according to an embodiment are given below with reference to FIGS. 9-11. In the embodiment, a WLED lamp of electrical power 20 Watt is employed and its polarized beam is regarded as random. Both the common-path interferometric unit and the carrier frequency modulation unit are adopted. The thickness of the birefringent crystal of the common-path interferometric unit is made of yttrium orthovanadate (YVO4), which predetermined as 630 micrometers and optimized for the spectrometer employed. The SPR and the LRSPR configurations are provided respectively for comparison purpose. The sensor layer structures are a thin gold layer with 48 nm thickness for the SPR configuration and a gold/silicon dioxide/gold multi-layer stack with thicknesses of 48 nm, 620 nm and 2 nm respectively for the LRSPR configuration. The results indicate that for a 1° spectral phase change the corresponding refractive changes are $8.53 \times 10^{-7}$ for the SPR configuration and $1.95 \times 10^{-8}$ MU for the LRSPR configuration. This means that the detection resolution of the LRSPR configuration is approximately 44 times higher than that of the SPR configuration. FIG. 10 and FIG. 11 show simulation results of the spectral phase response from the SPR and LRSPR configurations, respectively, when they are incorporated in the wide dynamic range phase-sensitive SPR sensor. The incident angles used in this simulation is fixed at about 73.5°, and the resultant signal traces are detected by a 3648-elements optical spectral analyzer covering 600 nm to 800 nm with approximately 0.05 nm interval for both SPR and LRSPR configurations. The curves (from curve 1001 to curve 1010) represent the spectral phase response of the sensing layer at each wavelength interval, which is the phase signal detected in each spectral element within the spectral analyzer. Specifically, the curves from curve 1001 to curve 1010 represent the spectral phase response of the sensing layer at the wavelengths of 655 nm, 660 nm, 665 nm, 670 nm, 674 nm, 679 nm, 684 nm, 689 nm, 694 nm and 699 nm, respectively. The phase response curve from the SPR configuration is shown in FIG. 10, the refractive index sensing range is from 1.333RIU to 1.375RIU (i.e. the dynamic range is approximately $4\times10^{-2}$ MU). The resolution gradually decreases from $3.57\times10^{-6}$ RIU/degree to $8.41\times10^{-5}$ RIU/degree as the refractive index moves further away from the optimized value. FIG. 11 shows the simulation results of the phase response in the wide dynamic range spectral phase-sensitive SPR sensor with the LRSPR sensing surface configuration. The curves from curve 1101 to curve 1115 represent the spectral phase response of the sensing layer at each wavelength interval, specifically, the wavelengths of 660 nm, 665 nm, 670 nm, 674 nm, 679 nm, 684 nm, 689 nm, 694 nm, 699 nm, 704 nm, 709 nm, 714 nm, 718 nm, 723 nm, 728 nm and 733 nm, respectively. The phase response of the LRSPR configuration, as shown in FIG. 11, indicates that the resolution only varies from $3.36\times10^{-8}$ RIU/degree to $7.73\times10^{-8}$ RIU/degree within the dynamic range of $4\times10^{-2}$ MU. Thus, the multi-wavelength spectral phase interrogating system is compatible with standard SPR and LRSPR configurations, resulting in tremendous expansion of the measurable dynamic range for both arrangements.

The polychromatic spectral phase-sensitive SPR sensor according to the present application has an advantage over the conventional monochromatic laser based phase-sensitive SPR scheme in terms of operational dynamic range of the refractive index measurement. It includes a broadband light source for providing a polychromatic light beam; a common-path spectral interferometer which provides simplified optical configuration and reduced fabrication cost in comparison to previous Michelson approach. In addition, an electronically controlled liquid crystal variable retarder can be provided to introduce carrier frequency modulation without mechanical moving part. Also, an SPR sensing unit, which is based on either an SPR or an LRSPR sensing layer configuration, can be adopted for receiving a multi-wavelength light beam at fixed angles of incident and introducing a specific phase retardation change in each incident wavelength within the polychromatic beam, and a single channel spectral analyzer unit can be provided for receiving the light emerging from spectral interferometer to provide a series of spectral oscillation for further processing to find the differential phase retardation introduced by the SPR sensor unit, which ultimately leads to the determination of the refractive index shift caused by the binding of biomolecules to the sensing surface. A processing unit can be provided for analyzing the interferometric signal traces generated from the recombination of the reference and signal polarized beams that finally the measured refractive index shift in the sensor surface. The introduction of a polychromatic light source in spectral phase-sensitive SPR sensor system drastically increases the detection dynamic range of the system. This also permits the incorporation of LRSPR sensor layer design, which is known to offer very high phase detection resolution because of its narrow resonance peak, so that the limited operational range can be compensated by the multi-wavelength approach. The resultant system therefore offers high measurement resolution and wide dynamic range in a robust optical configuration, which enables the system to be used in a range of biomedical detection applications.

The present application is based on the exploitation of wavelength dependent phase of a spectral interrogating SPR system via common-path carrier-frequency-modulated differential spectral interferometry. In order to achieve wide dynamic range, the polychromatic light source may be collimated and directed to the SPR sensing surface at fixed angles and covers a broad range of wavelengths. To facilitate high resolution of measurement, a carrier frequency modulator in terms of an electronically controlled liquid crystal variable retarder is implemented into the common interferometric path. The exit beam, which is now selectively modulated by SPW together with a carrier frequency modulation, in fact contains SPR information enclosed by the spectral bandwidth of the polychromatic source. Consequently, if an optical spectrum analyzer (OSA) is configured to collect the light energy of the entire reflected spectrum, the signal from individual detector elements is equivalent to conducting SPR detection with numerous carrier frequency modulated monochromatic sources. By implementation of spectral interferometry, the signal traces collected by the OSA contain the necessary information for finding both the spectral SPR reflectivity dip as well as the spectral SPR phase of the polychromatic spectrum simultaneously. This means it is possible to cover all the performance attributes of conventional spectral SPR systems, while at the same time further provides much improved resolution capability through carrier frequency modulated spectral phase-sensitive detection.

In the application, the use of polychromatic light source can increase the range of incident wavelengths so as to increase the dynamic range of phase-sensitive SPR biosensors. In addition, the introduction of LRSPR effect in the SPR sensing surface can sharpen the resonance peak so that the detection resolution of phase-sensitive SPR biosensors can be further enhanced. The SPR sensor of the present application provides the following advantages: It resolves the issue of limited dynamic range typically associated with monochromatic laser based phase-sensitive SPR biosensors. It resolves the issue of limited detection sensitivity typically associated with spectral intensity interrogating SPR biosensors. It overcomes the issue of spectral phase discontinuity associated with the sharp phase jump due to LRSPR configuration.

Therefore, the spectral interferometric SPR biosensor with the common-path scheme is possible to offer a robust optical configuration with reduces number of elements, i.e. eliminates the dummy SPR prism, thus reduces the manufacturing cost, while retaining the phase detection sensitivity.

Figure 12:
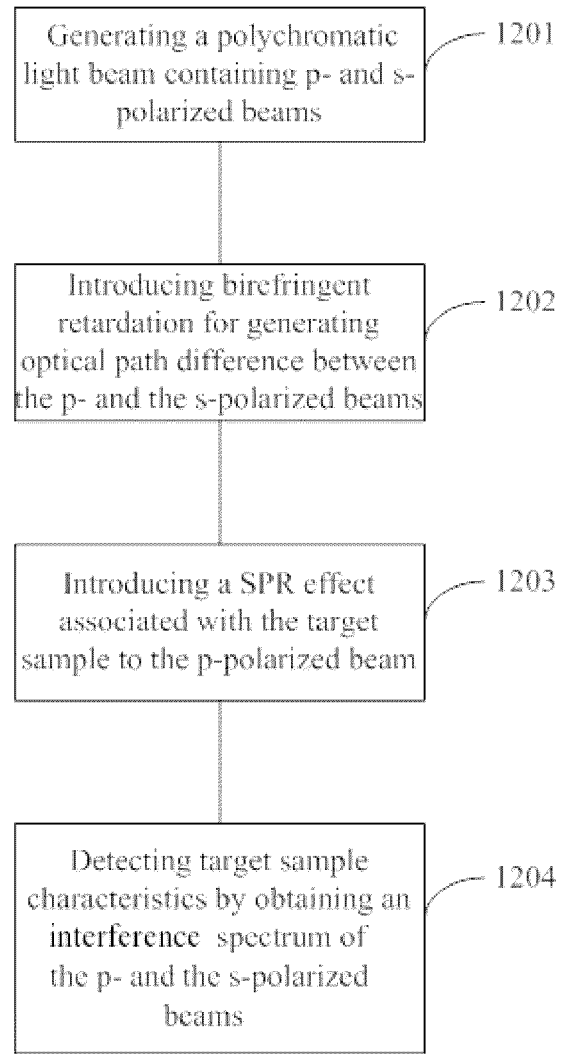
FIG. 12 is a flowchart of a method for detecting characteristics of a target sample according to an embodiment of the present application.

According to another aspect of the present application, a method for detecting characteristics of a target sample is provided as shown in FIG. 12. In step 1201, generating, by a source unit, a polychromatic light beam containing p-polarized beam and s-polarized beam. In step 1202, introducing, by an interferometric unit, birefringent retardation for generating optical path difference between the p-polarized beam and the s-polarized beam. In step 1203, introducing a SPR effect associated with the target sample to the p-polarized beam. In step 1204, detecting target sample characteristics by obtaining an interference spectrum of the p-polarized beam and the s-polarized beam from the SPR sensing unit.

According to an embodiment, an extra optical path difference is introduced between the p-polarized beam and the s-polarized beam at each wavelength, and the amount of the extra optical path difference is adjusted in time domain.

According to an embodiment, a beam of broad spectral range light containing random polarized beam is emitted by a source, the wavelengths of light beam emitted from the source is selected by a filter, the light beam is converted into parallel light beam with planar wavefront by a collimator, and a content ratio between the p-polarized and s-polarized components is selected by a polarizer.

According to an embodiment, the interference spectrum of the p-polarized beam and the s-polarized beam is obtained from the SPR sensing unit, and the target sample characteristics is determined by computing differential phase between the p-polarized beam and s-polarized beam through the obtained interference spectrum.

While the present application has been illustrated by the above description and embodiments or implementations, it is not intended to restrict or in any way limit the scope of the appended claims hereto.

What is claimed is:

1. An optical sensing device comprising:
a source unit configured to generate a polychromatic light beam containing p-polarized beam and s-polarized beam;
an interferometric unit, configured to introduce birefringent retardation for generating optical path difference between the p-polarized beam and the s-polarized beam;
a SPR sensing unit, configured to receive both p-polarized beam and s-polarized beam and induce a SPR effect to the p-polarized beam associated with a target sample;
a detection unit, detecting target sample characteristics by obtaining an interference spectrum of the p-polarized beam and the s-polarized beam from the SPR sensing unit,
wherein the interferometric unit comprises a birefringent crystal introducing the optical path difference between the p-polarized beam and s-polarized beam,
wherein the interferometric unit further comprises a carrier frequency modulation unit generating oscillation cycles in time domain, so as to introduce a carrier frequency modulation at each wavelength of the p-polarized beam and s-polarized beam,
wherein the carrier frequency modulation unit comprises:
a liquid crystal variable retarder introducing an extra optical path difference between the p-polarized beam and the s-polarized beam at each wavelength, and
an electronic controller adjusting amount of the extra optical path difference introduced by the retarder via controlling an external voltage or current source of the retarder.

2. The optical sensing device according to claim 1, wherein the source unit comprises:
a source emitting a beam of broad spectral range light containing random polarized beam;
a filter selecting the wavelengths of light beam emitted from the source;
a collimator converting the light beam into parallel light beam with planar wavefront; and
a polarizer selecting a content ratio between the p-polarized and s-polarized components.

3. The optical sensing device according to claim 2, wherein the source comprises: a quartz tungsten halogen (QTH) lamp, a solid state white-light emitting diode (WLED), a broadband superluminescent diode (SLD), a rare-earth-doped amplified spontaneous emission (ASE) source, or a supercontinuum generator for generating supercontinuum by propagation of ultrashort laser pulses in a microstructured optical fiber.

4. The optical sensing device according to claim 1, wherein the sensing unit comprises:
a prism;
a transducing layer coated on a surface of the prism to serve as a sensing surface; and
a sample flow chamber associated with the prism allowing the sample flowing through the sensing surface.

5. The optical sensing device according to claim 1, wherein the sensing unit is a long-range SPR sensing unit comprising:
a prism;
a transducing layer coated on a surface of the prism to serve as a sensing surface, wherein the transducing layer is made of a dielectric layer sandwiched by two conducting layer; and
a sample flow chamber associated with the prism for guiding a sample flowing over the sensing surface.

6. The optical sensing device according to claim 1, wherein the detection unit comprises:
an optical probe unit for obtaining an interference spectrum of the p-polarized beam and the s-polarized beam from the SPR sensing unit; and
a processing unit for determining the target sample characteristics by computing differential phase between the p-polarized beam and s-polarized beam through the obtained interference spectrum.

7. The optical sensing device according to claim 6, wherein the optical probe unit comprises:
a broadband linear polarizer for recombining the p-polarized beam and s-polarized beam from the SPR sensing unit so as to generate spectral interferograms; and
a prober configured to obtain the interference spectrum of the recombined light beam.

8. The optical sensing device according to claim 7, wherein the prober comprises:
a single channel spectral analyzer including a dispersive grating for separating the p-polarized beam and s-polarized beam into spatially dispersed wavelengths;
a detector array having a plurality of pixels, each pixel for measuring an intensity oscillation signal for a wavelength of the dispersed wavelengths.

9. The optical sensing device according to claim 8, wherein the detector array is a high density linear charge-coupled optoelectronic detector array to collect the spectral-temporal oscillation signal of the p-polarized beam and s-polarized beam.

10. A method for detecting characteristics of a target sample, comprising:
generating, from a source unit, a polychromatic light beam containing p-polarized beam and s-polarized beam;
introducing, by an interferometric unit, birefringent retardation for generating optical path difference between the p-polarized beam and the s-polarized beam;
introducing a SPR effect associated with the target sample to the p-polarized beam;
detecting target sample characteristics by obtaining an interference spectrum of the p-polarized beam and the s-polarized beam from the SPR sensing unit;
introducing, by a liquid crystal variable retarder, an extra optical path difference between the p-polarized beam and the s-polarized beam at each wavelength, and
adjusting amount of the extra optical path difference in time domain via controlling an external voltage or current source of the retarder.

11. The method according to claim 10, further comprising:
emitting, by a source, a beam of broad spectral range light containing random polarized beam;
selecting, by a filter, the wavelengths of light beam emitted from the source;
converting, by a collimator, the light beam into parallel light beam with planar wavefront; and
selecting, by a polarizer, a content ratio between the p-polarized and s-polarized components.

12. The method according to claim 10, further comprising:
obtaining an interference spectrum of the p-polarized beam and the s-polarized beam from the SPR sensing unit; and determining the target sample characteristics by computing differential phase between the p-polarized beam and s-polarized beam through the obtained interference spectrum.

* * * * *

UNITED STATES PATENT AND TRADEMARK OFFICE
CERTIFICATE OF CORRECTION

PATENT NO. : 8,953,168 B2
APPLICATION NO. : 13/492444
DATED : February 10, 2015
INVENTOR(S) : Shu Yuen Wu It is certified that error appears in the above-identified patent and that said Letters Patent is hereby corrected as shown below:

Specification

In column 1 at line 27 (approx.), Change "different" to --difference--.

In column 2 at line 29, Change "configuration; and" to --configuration;--.

In column 4 at line 29, Change "SRR" to --SPR--.

In column 4 at line 36, Change "(MU)" to --(RIU)--.

In column 4 at line 38, Change "MU" to --RIU--.

In column 6 at line 53, Change "MU" to --RIU--.

In column 7 at line 8, Change "MU)." to --RIU).--.

In column 7 at line 22, Change "MU." to --RIU.--.

Signed and Sealed this
Twenty-ninth Day of December, 2015

Michelle K. Lee
*Director of the United States Patent and Trademark Office*